United States Patent [19]

Pang et al.

[11] Patent Number: 4,966,893
[45] Date of Patent: Oct. 30, 1990

[54] METHOD FOR TREATMENT OF SENILE DEMENTIA

[76] Inventors: Peter K. T. Pang, 52225 Range Road 232, 205 Carriage Lane, Sherwood Park, Alberta, Canada, T8A 2A6; Lawrence C. H. Wang, 5012-144 St., Edmonton, Alberta, Canada, T6G 2E9; Christina G. Benishin, 218-53431 Range Rd 221, Androssan, Alberta, Canada, T0B 0E0; Hsing J. Liu, 3543-105 B St., Edmonton Alta., Canada, T6J 2K9

[21] Appl. No.: 297,012

[22] Filed: Jan. 13, 1989

[51] Int. Cl.$^5$ .................. A61K 35/78; C07H 15/20
[52] U.S. Cl. .................................. 514/54; 536/5; 514/879; 424/195.1
[58] Field of Search .......... 23/230 R; 536/5, 127, 536/128; 514/54, 879; 424/195.1

[56] References Cited

U.S. PATENT DOCUMENTS

| | | | |
|---|---|---|---|
| 4,157,894 | 6/1979 | Bombardelli | 536/5 |
| 4,317,816 | 3/1982 | Arichi et al. | 514/26 |
| 4,339,442 | 7/1982 | Takemoto et al. | 536/5 |
| 4,446,130 | 5/1984 | Hachiya et al. | 424/195.1 |
| 4,621,137 | 11/1986 | Miyake et al. | 536/6.3 |
| 4,647,460 | 3/1987 | Lee | 424/195.1 |
| 4,684,628 | 8/1987 | Liu | 514/824 |
| 4,687,761 | 8/1987 | Liu | 514/26 |
| 4,755,504 | 7/1988 | Liu | 536/6.3 |
| 4,814,339 | 3/1989 | Rotondo | 514/332 |
| 4,837,219 | 6/1989 | Hutterer | 514/400 |
| 4,847,082 | 7/1989 | Sabin | 514/102 |
| 4,851,414 | 7/1989 | Shiozaki et al. | 514/277 |

*Primary Examiner*—Ronald W. Griffin
*Attorney, Agent, or Firm*—Armstrong, Nikaido, Marmelstein, Kubovcik & Murray

[57] ABSTRACT

Ginsenosides $Rb_1$ and $Rg_1$ enhance the avaiability of acetylcholine in the cortical and hippocampal regions of the brain and alleviate the symptoms of Alzheimer-type senile dementia.

Pure $Rb_1$ is isolated from a mixture of ginsenosides by a process involving vacuum chromatography on silica gel. Preferably, the mixture of ginsenosides is enriched in $Rb_1$ by partition between an aqueous system and water ethyl acetatebutanol.

3 Claims, 3 Drawing Sheets

METHOD FOR TREATMENT OF SENILE DEMENTIA

This invention is directed to a method for alleviating the symptoms of senile dementia of the Alzheimer's type. In one specific aspect, the present invention is directed to an improved process for the isolation and purification of a ginsenoside useful in practicing that method.

BACKGROUND OF THE INVENTION

Senile dementia of the Alzheimer's type (SDAT) is widely recognized as a problem of increasing proportions in North America as well as around the world. The disease is associated with progressive physical and mental impairment to the point where the patient requires total care, and becomes a tremendous social and economic burden. Progress of the disease is believed to be related to degeneration of certain nerve tracts in the central nervous system, resulting in the loss of associated functions. Pathological studies indicate that brains of SDAT patients have loss of several neurotransmitter systems, related to different functions, but the system which is implicated the most is the cholinergic system. Studies show that several important cholinergic tracts innervating the cortical and hippocampal regions degenerate. Although this particular degeneration may not account for all of the symptoms of SDAT, it may account for the cognitive and memory deficits, which are some of the most difficult symptoms for patients and their families to deal with.

The pharmacological approaches which have been proposed for the managements of SDAT symptoms may be classified in two ways. The first is drugs which improve the function of existing neurons, especially to increase cholinergic nerve function. The second is drugs which decrease degeneration/increase regeneration of nerves.

Two types of drugs have been used in clinical trials to improve central cholinergic functions. The first is compounds which increase the availability of the existing endogenous neurotransmitter, acetylcholine (ACh); and the second is compounds which are exogenous, and mimic the effects of the endogenous transmitter at the receptor. However, these compounds exhibit side effects which limit their use.

It is generally believed that compounds which will increase the availability of the endogenous neurotransmitter are more desirable. Substances in this category are cholinesterase inhibitors, such as physostigmine and pyridostigmine, which decrease the breakdown of ACh, thus prolonging its functional lifetime at the crucial location, the synaptic cleft, and choline and lecithin, which increase the availability of the precursor for synthesis. Thus far other compounds have not been described which directly increase the availability of the endogenous neurotransmitter ACh by any other mechanisms, except by blockade of inhibitory presynaptic receptors (with e.g. atropine or clonidine), or by non-specific depolarization of nerves (e.g. veratridine).

Ginseng is the name given to the dried roots of the ginseng plants (genus Panax) and, more particularly, to extracts of those roots. The roots and their extracts contain a variety of substances including saponins and sapogenins.

Ginseng has been extensively used, mostly in Asia, as a tonic to promote health and well being, and as a medicine in the treatment of various disease conditions. The beneficial attributes of ginseng are attributed to its saponin content, a mixture of glucosides referred to collectively as ginsenosides.

DISCUSSION OF THE PRIOR ART

U.S. Pat. No. 4,157,894 to Bombardelli discloses the isolation of saponins from ginseng roots and the use of a purified concentrate in the geriatric field for elderly patients having difficulty in digesting less concentrated preparations. Bombardelli also discloses the structures of saponins $Rb_1$, $Rb_2$, Rc, Rd, Re, Rf and Rg.

U.S. Pat. No. 4,702,949 to Liu discloses a composition comprising 5-15% ginsenoside, 30-50% tetramethylpyrazine, 30-50% astragalan, and 5-15% atractylol in the treatment of cerebral vascular insufficiency and resultant paraplegia, hemiplegia and impaired neurofunction.

U.S. Pat. Nos. 4,157,894; 4,317,816; 4,446,130; 4,647,460; 4,684,628; 4,687,761; and 4,755,504 disclose the use of ginseng or ginseng extracts, alone, or in combination with other substances for various medically related purposes.

A procedure for the isolation of a crude mixture of ginsenosides from ginseng is described by J. Shoji, "Advances in Chinese Medicinal Materials Research", World Scientific Publishing Company, Singapore, pages 455-469 (1985). Material prepared by this established procedure is commercially available.

The preparation of ginseng extracts is also disclosed by Bombardelli and by Liu, discussed above, and in the other U.S. Patents listed above.

$Rb_1$ and $Rg_1$ have the structural formula:

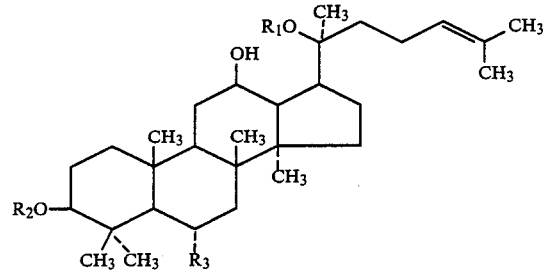

In $Rb_1$, $R_1$ is D-glucose B(1→6)D-glucose, $R_2$ is D-glucose B(1→2)D-glucose and $R_3$ is H. In $Rg_1$, $R_1$ is D-glucose, $R_2$ is H, and $R_3$ is O-D-glucose.

Existing procedures for the isolation and purification of ginsenoside $Rb_1$ include standard column chromatography, thin-layer chromatography, and high performance chromatography. These methods are laborious for the isolation of the compound in large quantities and often yield a low purity product.

BRIEF DESCRIPTION OF THE INVENTION

A primary object of the present invention is to provide a method for the treatment of senile dementia of the Alzheimer's type.

Another object of the invention is to provide an improved process for the isolation and purification of a ginsenoside used in that method for treating senile dementia.

We have discovered that ginsenosides $Rb_1$ and $Rg_1$ directly and selectively increase acetylcholine function in the brain and, accordingly, are useful in alleviating the symptoms of senile dementia.

In one specific aspect, the present invention is a method for alleviating the symptoms of Alzheimer-type senile dementia, which comprises administering to a mammal affected with Alzheimer-type senile dementia an amount of ginsenoside $Rb_1$ or of ginsenoside $Rg_1$ effective to increase the availability of acetylcholine in the cortical and hippocampal regions in the brain of the mammal.

In a second specific aspect, the present invention is a process for the isolation of ginsenoside $Rb_1$ which comprises the steps:

(a) dissolving a mixture of ginsenosides in methyl alcohol;

(b) adsorbing the mixture of ginsenosides on silica gel by contacting the solution of the mixture in methyl alcohol with the silica gel and evaporating the alcohol;

(c) placing the silica gel having the mixture of ginsenosides adsorbed thereon in a column for vacuum chromatography prepacked with silica gel;

(d) passing a mixture of chloroform and methyl alcohol through the columns to elute ginsenoside $Rb_1$; and (e) recovering ginsenoside $Rb_1$ from the chloroform and methyl alcohol eluate.

A mixture of ginsenosides enriched in $Rb_1$ particularly useful as the starting material in the process of the present invention may be obtained by:

(a) dissolving a mixture of crude ginsenosides obtained by extraction of ginseng in water;

(b) washing the aqueous solution of mixed ginsenosides with ethyl acetate;

(c) extracting the ethyl acetate-washed solution successively with a mixture of 4 volumes of ethyl acetate and 1 volume of 1-butanol, with 1 volume of ethyl acetate and 1 volume of 1-butanol, and with 1-butanol pre-saturated with water;

(d) combining the ethyl acetate-1-butanol and 1-butanol-water extracts; and (e) recovering a mixture of ginsenosides enriched in $Rb_1$ from the combined extracts.

The vacumm chromatographic process described above yields ginsenoside $Rb_1$ of good quality and can be adapted to the preparation of larger amounts of that ginsenoside. Exceptionally high purity $Rb_1$ can be obtained by using a mixture of ginsenosides enriched in $Rb_1$ as the starting material in the process.

DETAILED DESCRIPTION OF THE INVENTION

Figure 6:
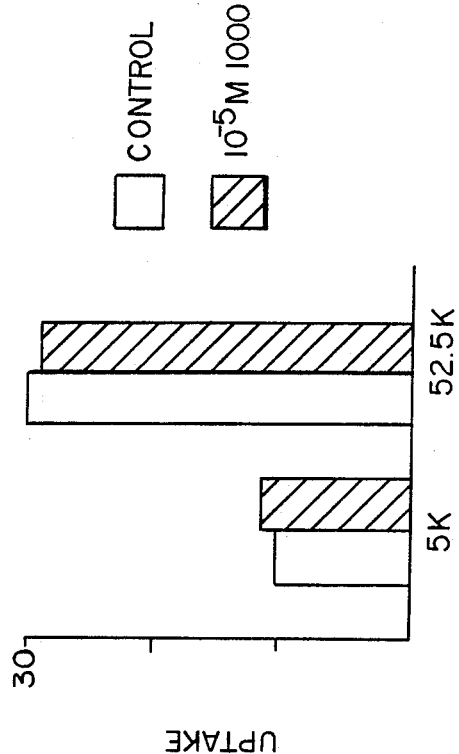
FIG. 6 is a graph of 45-Ca uptake at high and low concentrations of potassium.

Our invention is further illustrated by means of the following non-limiting examples:

EXAMPLE 1:

(isolation of $Rb_1$)

About 1 g of crude ginsenosides obtained by the procedure described by Shoji in "Advances in Chinese Medicinal Materials Research" was dissolved in 10 ml of methanol. The resultant solution was mixed with 10 g of silica gel (Merck 0.040–0.063 mm particle size, 230–400 mesh ASTM). The silica gel was air dried for about 1 hour and then placed in a column for vacuum chromatography, as described by Coll et al, Aust. J. Chem., 30, 1305 (1977), prepacked with 80 g of silica gel. Elution with a solution of chloroform and methanol (85:15) gave a fraction from which 75 mg of >98% pure $Rb_1$ was obtained. An additional 120 mg of $Rb_1$, purity about 60%, was recovered from other fractions of the eluate.

EXAMPLE 2:

(preparation of ginsenosides enriched in $Rb_1$)

600 mg of the crude mixture of ginsenosides obtained by the procedure of Shoji was dissolved in 100 ml water. The aqueous solution was washed with ethyl acetate ($2 \times 40$ ml) and then extracted with a solution of ethyl acetate and 1-butanol (4:1; $4 \times 40$ ml) followed by extraction with a 1:1 solution of ethyl acetate-1-butanol ($2 \times 40$ ml) and then 1-butanol presaturated with water ($2 \times 40$ ml). The last three extracts were combined and concentrated to give 140 mg of ginsenosides containing about 60% of $Rb_1$. Use of that enriched mixture as the starting material in Example 1 gave essentially pure $Rb_1$.

The following examples illustrate that $Rb_1$ and $Rg_1$ directly and selectively increase acetylcholine function in the brain and are useful in the treatment of Alzheimer-type senile dementia.

Figure 1:
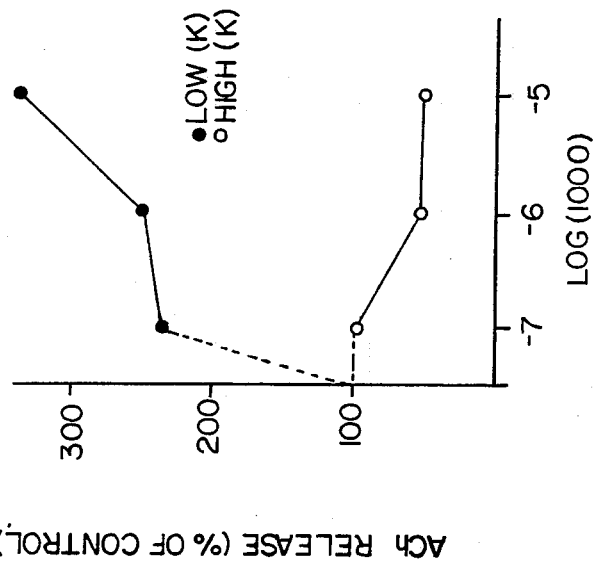
FIG. 1 is a graph of acetylcholine release plotted against log concentration $Rb_1$ at high and low concentrations of potassium.

EXAMPLE 3:

Pinched off nerve endings (synaptosomes) from whole rat brain were first incubated in the presence of the precursor $^3H$-choline, which is converted intracellularly to $^3H$-ACh. The release of ACh from synaptosomes was quantitated under low [K] and high [K] conditions intended to simulate physiological stimulation. The addition of $Rb_1$ increased the release of $^3H$-ACh as shown in FIG. 1.

Figure 2A:
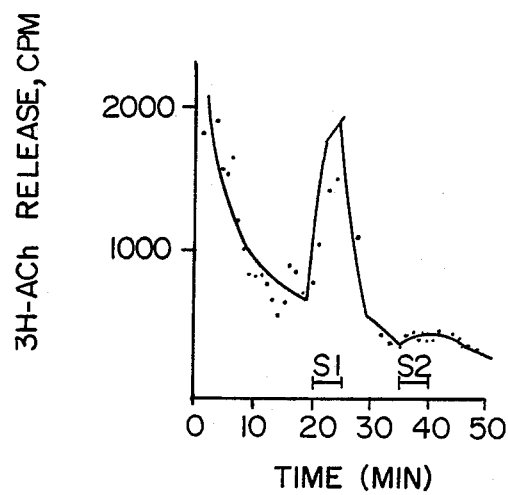
FIGS. 2 and 3 are graphs plotting electrically stimulated $^3H$-acetylcholine release against time.
Figure 2B:
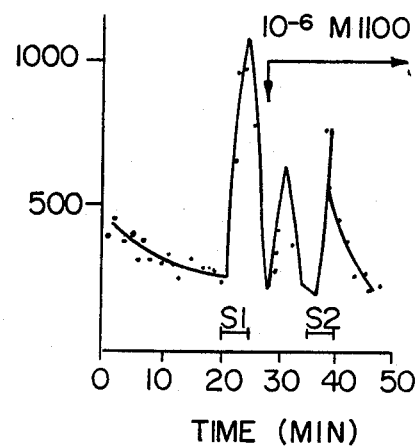
Figure 3A:
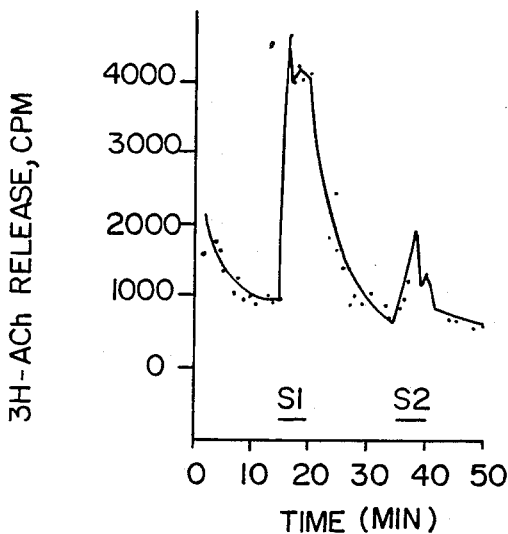
Figure 3B:
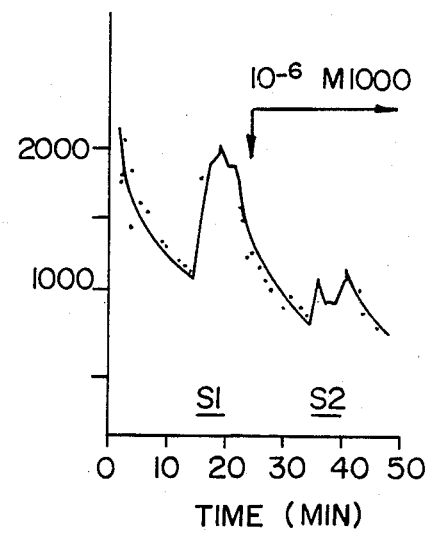

EXAMPLE 4:

Using a different protocol, synaptosomes, which had been previously incubated with $^3H$-choline, as in the first series of experiments, were continually perfused with HEPES-buffered Krebs solution. The release of ACh was effected by subjecting the synaptosomes to electrical field stimulation, which more closely mimics physiological stimulation. In FIGS. 2 and 3, the left panel shows the release pattern in the absence of any added drug, and the right panel shows the release pattern in the presence of $10^{-6}M$ drug during the last 25 minutes of perfusion. The results obtained by calculating the ratio of the amounts of ACh released during the two periods of electrical stimulation (the areas under the curves, S2/S1) indicate that both $Rb_1$ and $Rg_1$ increase the electrically stimulated release. In addition, $Rg_1$ stimulates the resting release of $^3H$-ACh, as indicated, by the increase in the resting efflux of $^3H$-ACh when the drug was first added. While the net amount of $^3H$-ACh released in each run can vary, depending on the amount of protein on the filter and aging of the synaptosomes, the S2/S1 ratio remains quite constant from run to run using a given chamber. Therefore, in each experiment the same chamber was used for both control and test-drug runs.

Figure 5:
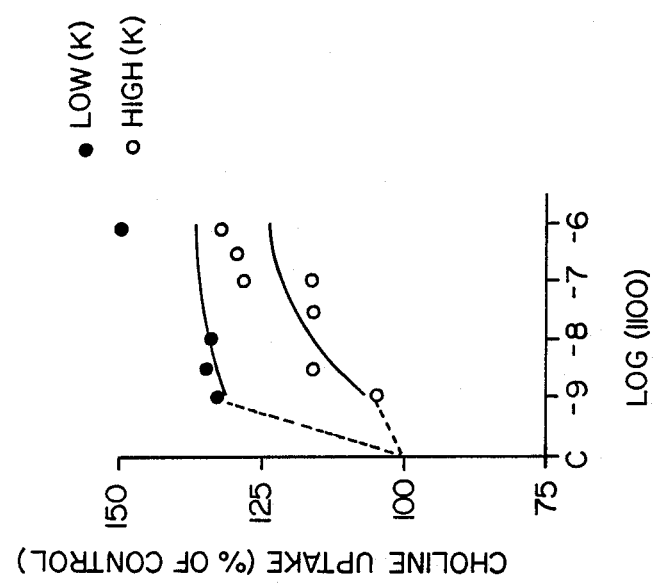
FIGS. 4 and 5 are a graphs of choline uptake plotted against log concentration $Rb_1$ and against log concentration $Rg_1$, respectively.
Figure 4:
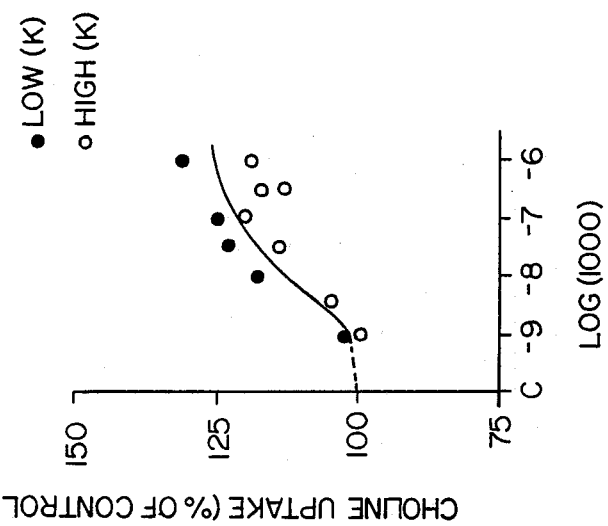

The stimulation of ACh release is also associated with an increase in the specific uptake of the precursor $^3$H choline as shown in FIGS. 4 and 5. Although the magnitude of stimulation of choline uptake is not as great as the magnitude of stimulation of ACh release, it is a consistent and significant effect, and can still quantitatively account for the increase in release. This suggests a general stimulation of brain cholinergic function. Further, preliminary experiments show that of three cholinergic brain regions examined, cortex, stratum, and hippocampus, stimulation of ACh release from synaptosomes is most pronounced in the hippocampus, a brain region strongly implicated in memory functions, and to a lesser extent in the cortex.

EXAMPLE 5:

This example confirms that $Rb_1$ and $Rg_1$ do not stimulate the release of neurotransmitter by non-selectively depolarizing nerve endings. The effects of $Rb_1$ on the resting and voltage dependent uptake of $^{45}$Ca into rat brain synaptosomes are shown in FIG. 6. These results indicate that the dramatic stimulation of $^3$H-ACh release is associated with only a minimal increase in the resting uptake of Ca, upon which ACh release is dependent. If this compound were acting as a non-specific depolarizing agent, one would predict the resting uptake of $^{45}$Ca would be stimulated several fold, to the same level as the depolarized (52.5 K) uptake.

When using $Rb_1$ and $Rg_1$ to alleviate the symptoms of Alzheimer-type senile dementia, $Rb_1$ and $Rg_1$ can be processed by conventional methods of galenic pharmacy into pharmaceutical preparations for oral or parenteral administration, e.g., to mammals including humans. Conventional excipients are pharmaceutically acceptable organic or inorganic carrier substances suitable for parenteral, enteral or topical application which do not deleterious react with $Rb_1$ or $Rg_1$. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with $Rb_1$ and $Rg_1$.

For parental application, particularly suitable are injectable sterile solutions, preferably oily or aqueous solutions, as well as suspensions, emulsions, or implants, including suppositories.

For enteral application, particularly suitable are tablets, dragees, suppositories or capsules having talc and/or sa carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein $Rb_1$ and $Rg_1$ is protected with differentially degradable coatings, e.g., by microencapsulation, multiple coatings, etc.

Depending on the type of mammal to which it is being administered, the daily dosage of $Rb_1$ or $Rg_1$ for a mammal weighing 50 kg is generally about 100–1000 mg, preferably administered 3 or 4 times a day in divided doses. Thus, a suitable dosage form would contain 25–250 mg of $Rb_1$ or $Rg_1$. Appropriate dosages and regimens for a given host can be determined using conventional considerations, e.g., by customary comparison of the differential activities of the subject compound and of a known agent, e.g., by means of conventional pharmacological protocols.

What is claimed is:

1. A method for alleviating the symptoms of Alzheimer senile dementia, which comprises administering to a mammal affected with Alzheimer senile dementia an amount of ginsenoside $Rb_1$ or of ginsenoside $Rg_1$ effective to increase the availability of acetylcholine in the cortical and hippocampal regions in the brain of the mammal.

2. A method according to claim 1, wherein the $Rb_1$ or $Rg_1$ is administered to the mammal in a daily dosage of 100–1000 mg.

3. A method according to claim 2, wherein the daily dosage is administered in portions 3 or 4 times per day.

* * * * *